United States Patent [19]

Dillon

[11] Patent Number: 5,057,013
[45] Date of Patent: Oct. 15, 1991

[54] DENTAL CORTICAL PLATE PERFORATOR

[76] Inventor: Frank J. Dillon, 39 Eglington Rd., Donnybrook, Dublin 4, Ireland

[21] Appl. No.: 188,966

[22] Filed: May 2, 1988

[30] Foreign Application Priority Data

May 19, 1987 [IE] Ireland .................................. 1308/87

[51] Int. Cl.$^5$ ............................................... A61C 3/02
[52] U.S. Cl. .................................... 433/165; 433/134; 606/80
[58] Field of Search ....................... 433/165, 166, 134; 606/80, 167, 172, 180, 185

[56] References Cited

U.S. PATENT DOCUMENTS 3,534,476 10/1970 Winters .............................. 433/165
4,021,917 5/1977 Nakanishi ........................... 433/165

Primary Examiner—Cary E. Stone

[57] ABSTRACT

A dental apparatus for perforating the cortical plate of human maxillary and mandibular bones comprises a solid metal needle moulded into a plastic shank, the shank being formed with means for cooperation with a dental contra-angle or straight handpiece into which the shank may be inserted. The shank has a collar at its front end, and a hollow protective cap is removably fitted over the exposed needle and engages the collar.

6 Claims, 1 Drawing Sheet

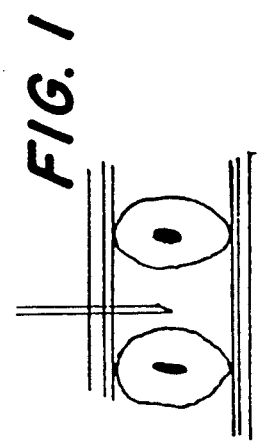
FIG. 1
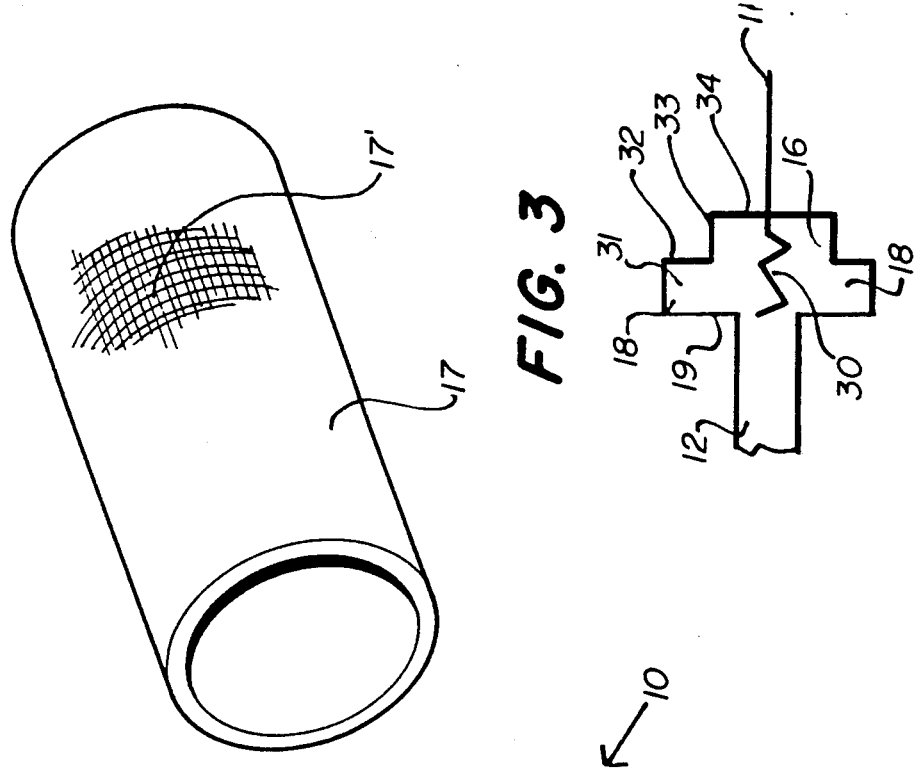
FIG. 2
FIG. 3
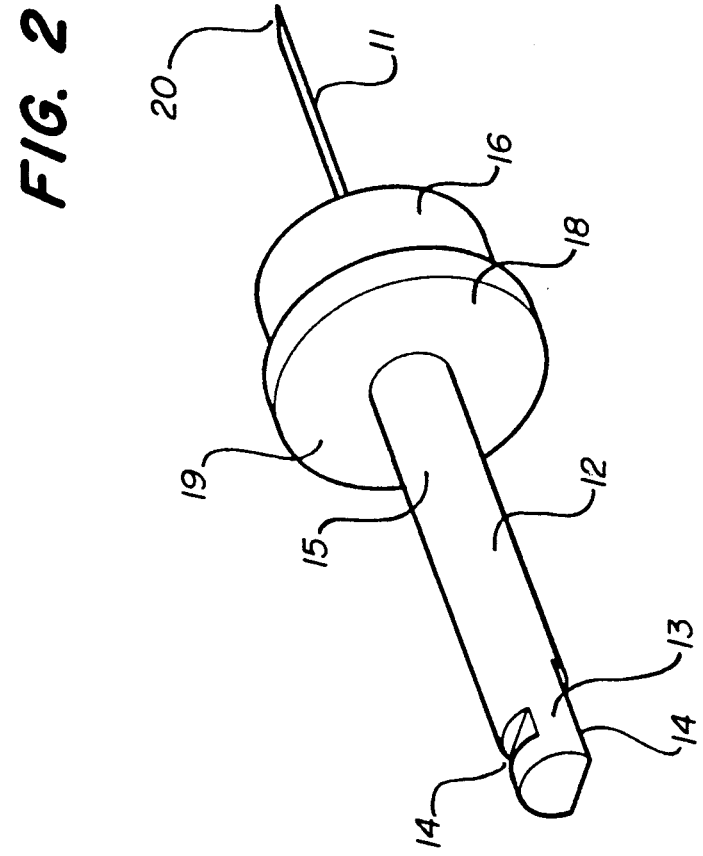

DENTAL CORTICAL PLATE PERFORATOR

The present invention relates to a dental apparatus for cortical plate perforation.

There are a variety of methods and apparatus currently in use for providing local anaesthesia in dentistry. These methods and apparatus, however, all have disadvantages either being difficult for a dentist to perform or being painful or unpleasant for the patient.

For example, in the infiltration method, a local anaesthetic solution is injected into soft tissue adjoining a tooth and disperses around that area. In doing so, the anaesthetic passes through the cortical plate of bone and thus affects the nerve bundle entering the tooth. This method has numerous disadvantages some of which include the delay between injection and effect, the long duration of the effect and the ballooning of tissues.

In the regional block method of injection the local anaesthetic solution is injected around the nerve trunk as it enters the bone, thus anaesthetising all of the areas served by that trunk. This technique also has disadvantages which include the fact that it is difficult to locate the nerve trunk accurately, the injections are uncomfortable, and there is a delay between injection and effect.

Other techniques include the intraligamentry method, mandibular and maxillary anaesthesia all of which have disadvantages.

Intra-osseous anaesthesia is a technique which has been used to anaesthetise teeth by injecting local anaesthetic solution into the cancellous bone around the apex of the tooth. In order to do this, access must be gained through the cortical layer of bone and into the cancellous bone.

Intra-osseous anaesthesia (FIG. 1) is a desirable technique as among its many advantages it provides instant anaesthesia and profound pulpal anaesthesia, the effect may be localised and only a small dose of anaesthetic solution is required. However, as the cortical plate is very hard it is difficult to perforate.

At present two types of apparatus have been used to perform intra-asseous anaesthesia. These are a surgical bur used to perforate the cortical plate and the villette injector.

The use of a surgical bur has disadvantages in that burs are expensive and they have to be sterilised between uses or a new bur used each time. In addition, the method is slow requiring the attached gingiva and periosteum to be anaesthetised before the cortical plate is perforated.

The villette injector is an apparatus that serves as both a perforator and an injector. It uses specially designed needles on the front end of the instrument and a conventional dental motor attached at the rear of the instrument. The needles used are hollow and as the required region is perforated, the needle often becomes clogged with pulverised bone which prevents the injection of the anaesthetic solution.

It is often difficult to remove the clogging material from the needle thus often necessitating the use of a second needle. Other disadvantages of this method include, the initial capital cost of the instrument purchase, the particular needles are expensive, and the design of the instrument makes access to various parts of the mouth difficult if not impossible.

Therefore, it is an object of the present invention to mitigate the above problems and disadvantages of delivering dental anaesthetics.

According to the present invention there is provided a dental apparatus for perforating the cortical plate of human maxillary and mandibular bones, comprising a solid metal needle fixed in a shank, and collar means on the shank adjacent to the needle, the shank being formed with means for cooperation with and fixing of the shank into a dental handpiece.

In a preferred form of the invention the apparatus is disposable and there is provided a collar on the front end of the shank which is adapted to receive a hollow cap which protects the needle prior to use.

Preferably, the shank has a second collar immediately behind the first collar, the second collar in use abutting the front end of the dental handpiece to prevent any residue in the dental handpiece from falling onto the sterile needle.

The needle is preferably of the standard gauge for dental needles, typically about 27 gauge thickness, and has a sharp bevelled free end.

An embodiment of the invention will now be described by way of example with reference to the accompanying drawings in which;

FIG. 1 is a drawing illustrating intra-osseous anaesthesia;

FIG. 2 is a perspective view of an embodiment of a dental apparatus for cortical plate perforation; and FIG. 3 is a diagrammatic cross-sectional view of the apparatus of FIG. 2.

In the drawing, the cortical plate perforator is generally indicated at 10 and comprises a cylindrical metal needle 11 fixed coaxially in a cylindrical shank 12. The rear end 13 of the shank 12 has formed therein suitable recesses 14 for cooperation with and fixing of the shank into a conventional dental contra-angle or straight handpiece. At the front end 15 of the shank there is provided an enlarged collar 16 which is an interference fit with the open end of a hollow protective cap 17 for the needle 11. A second collar 18 is provided immediately behind the first collar, the second collar 18 being of a substantially larger diameter than the first collar 16. The surface 19 of the second collar in use abuts the front end of the dental handpiece (not shown) to prevent any debris in the handpiece from falling into a patient's mouth. The cap 17 is preferably formed of a hard rubber or plastics material and has a roughened outer surface 17' to facilitate gripping. The needle 11 is solid (i.e. it is not hollow) and has a sharp bevelled free end 20. The shank 12 is preferably moulded of a plastics material and the needle 11 is preferably fixed in the shank 12 during the moulding of the shank. As shown in FIG. 3 the end 30 of the needle 11 which is fixed in the shank 12 is preferably bent into a double 'V' shape which ensures that the needle 11 does not rotate relative to the shank 12 during use. It is important that the needle 11 is rigidly fixed in the shank 12 and it has been found that the crimping of the end 30 of the needle 11 into the double 'V' shape provides the optimum securement of the needle 11 relative to the shank 12.

The apparatus has as a main advantage the fact that it can be manufactured very inexpensively and the apparatus can therefore be disposable. The apparatus may be sold with the needle 11 sterilised and covered by the cap 17, and the shank 12 can be inserted into the dental handpiece by holding the end cap 17. Once the apparatus is fixed into the handpiece the cap 17 may be removed to expose the sterile needle 11. Thus, the needle 11 will remain sterile until use.

The hollow cap 17 is also useful for removing the apparatus from the dental handpiece after use. Therefore, after use, the hollow cap 17 is readily engaged on the collar 16 and with the needle 11 protected the apparatus is removed from the dental handpiece and disposed. Thus, the cap 17 provides a means whereby the apparatus may be removed from the dental handpiece without any risk of the user being in contact with body fluids which will be present on the needle 11 after use. This is extremely important particularly since there may be a risk of contracting aids or hepatitis should a user accidentally prick a finger with the needle 11. It is therefore desirable that the cap 17 should be of a hard or rigid rubber or plastics material not easily penetrated by the needle 11. Moreover, for ease of operation the internal diameter of the cap 17 and the diameter of the corresponding collar 16, should be as large as possible and preferably be of a diameter of between 2 to 20 times greater than the diameter of the needle 11.

Another advantage of the collar 16 is that it provides a stop to limit the depth of penetration of the needle 11. Thus, the exposed length of the needle is preferably of a length between 5 mm and 15 mm and more preferably 8 mm, and the collar 16 in use acts to limit the depth of penetration of the needle 11, the depth of penetration being determined by the length of the exposed part of the needle.

A further advantage of the invention is that the two collars 16,18 combine to form a barrier to prevent bacterial contamination of the needle 11. Thus, the apparatus is supplied with the needle 11 sterilised and protected by the cap 17. However, the shank 12 and the surface 19 of collar 18 and the outer annular surface 31 are exposed. To contaminate the needle 11, any bacteria which may be present on surfaces 19 or 31 would have to change direction once through 90° to travel along surface 32, change direction again through 90° to travel along surface 33 and change direction a third time through 90° and travel along surface 34 before it could reach the needle 11. However, it is believed that bacteria are reluctant to change direction through 90° and since in the present apparatus they would have to make this change of direction some three times, the collars 16,18 provide in effect a bacterial barrier which serves to prevent or minimise the risk of contamination of the needle 11.

The following technique should be used:
1. Select a site for injection.
2. Disinfect and topically anaesthetise the attached gingiva over the injection site.
3. Place the bevel of a standard gauge needle against the attached gingiva, and inject a small amount of local anaesthetic until a slight blanching of the tissues is observed. This will anaesthetise the attached gingiva and the periosteum.
4. Place a cortical plate perforator 10 in a contra-angle or straight dental handpiece and remove the cap 17.
5. Hold the cortical plate perforator 10 with the needle 11 against and perpendicular to the cortical plate, and perforate the plate by rotating and gently pressing the perforator. It is easy, with practice, to tell when this is done because there is a sudden "give" when the plate is perforated.
6. Remove the perforator.
7. Insert a standard gauge needle into the perforation and inject the required amount of local anaesthetic.

The apparatus therefore allows the ready perforation of the cortical plate after which a conventional dental needle is used to inject a small amount of anaesthetic solution, directly to the region to be anaesthetised. As the anaesthetic is delivered directly to the required region only a small amount of solution is required which is quick acting.

The apparatus has been found to be extremely useful in that it enables a procedure to be followed to deliver an anaesthetic to a patient with the following advantages:

It gives GUARANTEED PROFOUND PULPAL ANAESTHESIA;
It is quick acting;
It uses only a minimum dose of local anaesthetic;
It is easy to administer;
It is inexpensive;
It does not cause ballooning of tissues;
It does not leave the patient numb for hours afterwards;
It does not involve risk of haematoma or trimus;
It permits work in all parts of the mandible at each session;
It dispenses with the need for a palatal injection;
It is relatively painless;

I claim:

1. A dental apparatus for perforating the cortical plate of human maxillary and mandibular bones, comprising a solid metal needle fixed in a shank, the shank being formed with means for cooperation with and fixing of the shank into a dental handpiece, the shank having a collar at its front end, and a hollow protective cap removably fitted over the exposed needle and engaging the collar.

2. An apparatus to claim 1, wherein the shank has a further collar at its front end behind the firstmentioned collar, the further collar serving to abut against the front end of a dental handpiece into which the shank may be inserted.

3. An apparatus according to claim 1, wherein the needle has a bevelled free end.

4. An apparatus according to claim 3, wherein the needle is of approximately 27 gauge thickness.

5. An apparatus according to claim 1, wherein the shank is of moulded plastics material and the rear end of the needle is moulded into the shank.

6. A method of perforating the cortical plate of human maxillary and mandibular bones in dental treatment, comprising providing a sterile solid metal needle fixed in a shank, the shank being formed with means for cooperation with and fixing of the shank into a dental handpiece, the shank having a collar at its front end, and a hollow protective cap removably fitted over the exposed needle and engaging the collar, inserting and fixing the shank into a dental handpiece, removing the protective cap, placing the needle against the cortical plate, and perforating the cortical plate by rotating the needle.

* * * * *